United States Patent
Brown et al.

(10) Patent No.: US 11,813,071 B2
(45) Date of Patent: Nov. 14, 2023

(54) APPARATUS AND METHODS FOR DETERMINING ELECTRICAL CONDUCTIVITY OF TISSUE

(71) Applicant: THE UNIVERSITY OF SHEFFIELD, Sheffield (GB)

(72) Inventors: Brian Brown, Sheffield (GB); Dilichukwu Anumba, Sheffield (GB)

(73) Assignee: THE UNIVERSITY OF SHEFFIELD, Sheffield (GB)

( * ) Notice: Subject to any disclaimer, the term of this patent is extended or adjusted under 35 U.S.C. 154(b) by 808 days.

(21) Appl. No.: 16/065,339

(22) PCT Filed: Dec. 21, 2016

(86) PCT No.: PCT/GB2016/054013
§ 371 (c)(1),
(2) Date: Jun. 22, 2018

(87) PCT Pub. No.: WO2017/109484
PCT Pub. Date: Jun. 29, 2017

(65) Prior Publication Data
US 2021/0161460 A1    Jun. 3, 2021

(30) Foreign Application Priority Data

Dec. 22, 2015  (GB) ..................... 1522661
May 16, 2016  (GB) ..................... 1608600

(51) Int. Cl.
*A61B 5/00*    (2006.01)
*A61B 5/0536*  (2021.01)
(52) U.S. Cl.
CPC ............ *A61B 5/435* (2013.01); *A61B 5/0536* (2013.01); *A61B 2562/0223* (2013.01)

(58) Field of Classification Search
CPC .. A61B 5/00; A61B 5/05; A61B 5/435; A61B 5/0536; A61B 2562/0223;
(Continued)

(56) References Cited

U.S. PATENT DOCUMENTS 5,521,609 A * 5/1996 Desch .................. H01Q 7/08
                                         343/788
6,549,800 B1 * 4/2003 Atalar .................. H01Q 1/40
                                         600/424
(Continued)

FOREIGN PATENT DOCUMENTS

GB         2500216       9/2013
WO      2006/129108     12/2006
(Continued)

OTHER PUBLICATIONS

Zeng ["A High-Temperature RF SQUID System for Magnetocardiography" Measurement Science and Technology, 1998]. (Year: 1998).*
(Continued)

*Primary Examiner* — Oommen Jacob
(74) *Attorney, Agent, or Firm* — Meunier Carlin & Curfman LLC

(57) ABSTRACT

Apparatus for determining the electrical conductivity of target cervical tissue using magnetic impedance spectroscopy comprising: an excitation coil for producing a magnetic field which is capable of inducing currents in the target cervical tissue; a gradiometer for detecting perturbations in said magnetic field caused by said induced currents, the gradiometer including screening means for minimising sensitivity to tissues other than the target tissue; processing means for determining an electrical conductivity of said target cervical tissue from said perturbations.

21 Claims, 15 Drawing Sheets

(58) Field of Classification Search
CPC .......... G01R 33/3657; G01R 33/34053; G01R 33/34084; G01R 33/287; H01Q 1/40; H01Q 1/44; H01Q 1/36; H01Q 11/08; H01Q 1/42; H01Q 1/362; A61M 25/09

See application file for complete search history.

(56) References Cited

U.S. PATENT DOCUMENTS

| | | | | |
|---|---|---|---|---|
| 6,675,033 | B1* | 1/2004 | Lardo | G01R 33/287 324/309 |
| 8,624,584 | B2* | 1/2014 | Krozer | G01R 33/12 436/526 |
| 9,844,347 | B2* | 12/2017 | Subramaniam | A61B 5/05 |
| 2002/0071121 | A1* | 6/2002 | Ortyn | C12Q 2563/179 356/419 |
| 2002/0101241 | A1* | 8/2002 | Chui | G01R 33/34084 324/319 |
| 2003/0028095 | A1* | 2/2003 | Tulley | G01R 33/3657 600/422 |
| 2004/0174154 | A1* | 9/2004 | Butters | H01Q 7/08 324/71.1 |
| 2004/0196037 | A1* | 10/2004 | Xiang | G01R 33/60 324/300 |
| 2005/0283067 | A1* | 12/2005 | Sobe | A61B 5/06 600/409 |
| 2008/0312713 | A1* | 12/2008 | Wilfley | A61B 18/1492 607/41 |
| 2010/0219820 | A1* | 9/2010 | Skidmore | A61B 5/6814 324/247 |
| 2011/0004076 | A1* | 1/2011 | Janna | H01Q 1/02 600/302 |
| 2015/0371768 | A1* | 12/2015 | Graham | H02J 7/0044 320/108 |
| 2018/0143150 | A1* | 5/2018 | Bezemer | A61B 5/7214 |
| 2021/0161460 | A1* | 6/2021 | Brown | A61B 5/435 |

FOREIGN PATENT DOCUMENTS

| | | |
|---|---|---|
| WO | 2006/129116 | 12/2006 |
| WO | 2015/185398 | 12/2015 |

OTHER PUBLICATIONS

Zakaria ["Advancements in Transmitters and Sensors for Biological Tissue Imaging in Magnetic Induction Tomography" Sensors 2012, 12, 7126-7156] (Year: 2012).*

Griffiths [Magnetic induction tomography, Meas. Sci. Technol. 12 (2001) 1126-1131]. (Year: 2001).*

Abdul [The use of electrical impedance spectroscopy in the detection of cervical intraepithelial neoplasia, International Journal of Gynecologic Cancer 2006;16:1823-1832.] (Year: 2006).*

Casanas, R. et al. "Biological tissue characterization by magnetic induction spectroscopy (MIS): requirements and limitations", IEEE Transactions on Biomedical Engineering, IEEE Service Center, Piscataway, NJ, vol. 50, No. 7, Jul. 7, 2003, pp. 871-874.

Zulkarnay, Z. et al. "Advancements in Transmitters and Sensors for Biological Tissue Imaging in Magnetic Induction Tomography", vol. 12, No. 12, Dec. 29, 2012, pp. 7126-7156.

Barai, A. et al. "Magnetic induction spectroscopy: non-contact measurement of the electrical conductivity spectra of biological samples", Measurement and Science Technology, IOP, Bristol, GB, vol. 23, No. 8, Jun. 25, 2012, pp. 88501.

Abdul, S. et al. "The use of electrical impedance spectroscopy in the detection of cervical intraepithelial neoplasia", International Journal of Gynecological Cancer, vol. 16, No. 5, Sep. 1, 2006, pp. 1823-1832.

International Search Report and Written Opinion dated Mar. 17, 2017, from International Application No. PCT/GB2016/054013, 16 pages.

Avis, J. et al. "In vitro multifrequency electrical impedance measurements and modelling of the cervix in late pregnancy". Physiol Meas 17Suppl 4A:A97 (1996).

Brown, B. et al. "Relation between tissue structure and imposed electrical current flow in cervical neoplasia", Lancet 355(9207):892 (2000).

Gandhi, S. et al. "Comparison of human uterine cervical electrical impedance measurements derived using two tetrapolar probes of different sizes", Biomed Eng Online 5:62 (2006).

Gandhi, S. et al. "Electrical impedance spectroscopy of the cervix in non-pregnant and pregnant women", Eur J Obstet Gynecol ReprodBiol 129:145 (2005).

Scharfetter, H. et al. "Biological Tissue Characterization by Magnetic Induction Spectroscopy (MIS): Requirements and Limitations", IEEE Transactions on Biomedical Engineering, vol. 50, No. 7, Jul. 2003.

Hoe, Y. et al. "Measuring Bioimpedance in the Human Uterine Cervix: Towards Early Detection of Preterm Labor", Proceedings of the 26th Annual International Conference of the IEEE EMBS, Sep. 1-5, 2004, pp. 2368-2372.

Jokhi, R.P. et al. "The role of cervical Electrical Impedance Spectroscopy in the prediction of the course and outcome of induced labour", BMC Pregnancy and Childbirth, 9:40, Sep. 2, 2009, pp. 1-8.

Jokhi, R.P. et al. "Reproducibility and repeatability of measuring the electrical impedance of the pregnant human cervix—the effect of probe size and applied pressure", BioMedical Engineering Online, 8:10, Jun. 17, 2009, pp. 1-11.

C H Riedel et al, "Planar system for magnetic induction conductivity measurement using a sensor matrix", 2004 Physiol. Meas. 25 403.

Yu, ZZ, Peyton, AT, Beck, MS, Conway, WF & Xu, LA 1993, 'Imaging system based on electromagnetic tomography (EMT)', Electronics Letters, vol. 29, No. 7, pp. 625-626.

* cited by examiner

| Probe type | Air cored | | Ferrite cored | | Ferrite core only | Ferrite screen only |
|---|---|---|---|---|---|---|
| | Measured | Simulated | Measured | Simulated | Simulated | Simulated |
| Norm. signal from surroundings | 1.65 | 1.43 | 0.38 | 0.31 | 0.71 | 0.83 |

APPARATUS AND METHODS FOR DETERMINING ELECTRICAL CONDUCTIVITY OF TISSUE

TECHNICAL FIELD

The present disclosure relates to the field of apparatus and methods for determining the electrical conductivity of human or animal tissue and particularly, but not exclusively, to apparatus and methods for determining the likelihood of preterm birth.

BACKGROUND

Premature delivery is the cause of perinatal death of two-thirds of babies that have no structural abnormalities. It poses a huge economic burden on scarce health resources as each very premature baby born costs several tens of thousands of pounds in neonatal care. When born before 28 weeks gestation, 1 in 4 babies develop disability. These disabilities can cost hundreds of thousands of pounds annually to treat. The families also suffer huge psychosocial burdens, one parent often having to give up work to care for a disabled child. Whilst survival of premature babies is improving, the rate of premature delivery is increasing, currently running at 7-12% of all births. There is no reliable means of identifying women who deliver prematurely. Current methods for identifying women at high risk of delivering prematurely such as ultrasound of the cervix and fetal fibronectin determination have limited accuracy in women who have no history of preterm birth. A technique for reliably predicting preterm birth by universal screening is therefore highly desirable.

Electrical impedance spectroscopy (EIS) is a known technique that can be used for assessing cervical pre-cancer as set out in, for example, WO2006/129108 (Brown and Tidy) and WO 2006/129116 (Brown and Tidy). Other publications concerning EIS for cervical investigations include:

Avis (1996). In vitro multifrequency electrical impedance measurements and modelling of the cervix in late pregnancy. Physiol Meas 17Suppl 4A:A97

Brown (2000). Relation between tissue structure and imposed electrical current flow in cervical neoplasia. Lancet 355(9207):892

Gandhi (2006). Comparison of human uterine cervical electrical impedance measurements derived using two tetrapolar probes. Biomed Eng Online 5:62

Gandhi (2006). Electrical impedance spectroscopy of the cervix in non-pregnant and pregnant women. Eur J Obstet Gynecol ReprodBiol 129:145

Jokhi (2009). Reproducibility and repeatability of measuring the electrical impedance of the pregnant human cervix. Biomed Eng Online 8:10; and Jokhi (2009). The role of cervical Electrical Impedance Spectroscopy in the prediction of the course and outcome of induced labour. BMC Pregnancy Childbirth 9:40.

The applicant has investigated the value of using EIS to measure the "resistance" of the cervix to very small electrical currents (in other words, the electrical conductivity of the cervical tissue) to detect changes that may precede premature birth. A serial pilot study of women at high risk of preterm birth showed predictive accuracy for premature delivery before 37 and 34 weeks. However significant measurement error was observed using the EIS technique and it is desired to improve accuracy and repeatability of the measurements. One possible reason for measurement error in the EIS technique is that it is difficult to ensure consistent pressure on the cervical tissue by the EIS probe. The mucus layer on the cervix affects tissue electrical conductivity, adding further error.

It is an aim of the present invention to address disadvantages associated with the known prior art.

BRIEF SUMMARY OF THE DISCLOSURE

Aspects and embodiments of the invention provide apparatus and methods as claimed in the appended claims.

According to an aspect of the invention there is provided —apparatus for determining the electrical conductivity of target cervical tissue using magnetic impedance spectroscopy comprising:

excitation means for producing a magnetic field which is capable of inducing currents in the target cervical tissue;

detection means for detecting perturbations in said magnetic field caused by said induced currents, the detection means including screening means for minimising sensitivity to tissues other than the target tissue;

processing means for determining an electrical conductivity of said target cervical tissue from said perturbations.

According to another aspect of the invention there is provided apparatus for determining the electrical conductivity of target human or animal tissue using magnetic impedance spectroscopy comprising:

excitation means for producing a magnetic field which is capable of inducing currents in the target human or animal tissue;

detection means for detecting perturbations in said magnetic field caused by said induced currents, the detection means including screening means for minimising sensitivity to tissues other than the target tissue;

processing means for determining an electrical conductivity of said target human or animal tissue from said perturbations.

Preferably, said excitation means and said detection means are arranged co-linearly with the target tissue at one end thereof. Preferably, in use, the target tissue is not located between said excitation means and said detection means.

In an embodiment, said excitation means is an excitation coil and said detection means is a gradiometer. Alternatively, said excitation means is a gradiometer and said detection means is a coil.

In an embodiment, said gradiometer comprises at least two gradiometer sensing coils for detecting perturbations in said magnetic field caused by said induced currents.

Alternatively, said gradiometer comprises a magnetoresistive device for detecting perturbations in said magnetic field caused by said induced currents.

In an embodiment, said screening means comprises ferrite or other high permeability material screening and/or concentric ferrite or other high permeability material mouldings.

The apparatus may further comprise a ferrite core on which said excitation coil and said gradiometer sensing coils are wound.

In an embodiment, said excitation coil comprises copper wire of 0.2 mm thickness and/or may comprise 30 turns.

Said gradiometer sensing coils may comprise copper wire of 0.1 mm thickness and/or may each comprise 40 turns. In an embodiment, the gradiometer sensing coils are equidistant from said excitation coil.

Preferably, the maximum outer diameter of the apparatus is less than 30 mm.

The apparatus may further comprise a housing for the excitation means and detection means, preferably made from PEEK or machinable ceramic and further preferably containing electric field screening such as a metalized polymer film or a conductive paint layer.

The apparatus may further comprise a handle, optionally wherein at least part of said processing means is contained within said handle.

In an embodiment, said processing means has a sampling rate of 100 million samples per second.

According to another aspect of the invention there is provided a method of determining the electrical conductivity of target human or animal tissue using magnetic impedance spectroscopy comprising the steps of:

placing excitation means close to the target tissue;
energising said excitation means to produce a magnetic field which is capable of inducing currents in the target tissue;
using detection means to detect perturbations in said magnetic field caused by said induced currents;
determining an electrical conductivity of said target human or animal tissue from said perturbations.

In an embodiment said target human or animal tissue is cervical tissue.

Further features are defined in the appended claims.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend an originally filed claim to depend from and/or incorporate any feature of any other claim although not originally claimed in that manner.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWINGS

One or more embodiments of the invention will now be described, by way of example only, with reference to the accompanying drawings in which:

FIG. 14(a) shows results from magnetic shielding for surrounding tissues at drive frequencies of 100 kHz with 1.0 $Sm^{-1}$ saline filled to different depths of the cylinder which surrounded the air-cored (line 207) and ferrite-cored (line 208) MIS probes;
FIG. 14(b) shows the maximum contribution from surrounding tissues for the experiments shown in FIG. 14a.

DETAILED DESCRIPTION

Figure 1:
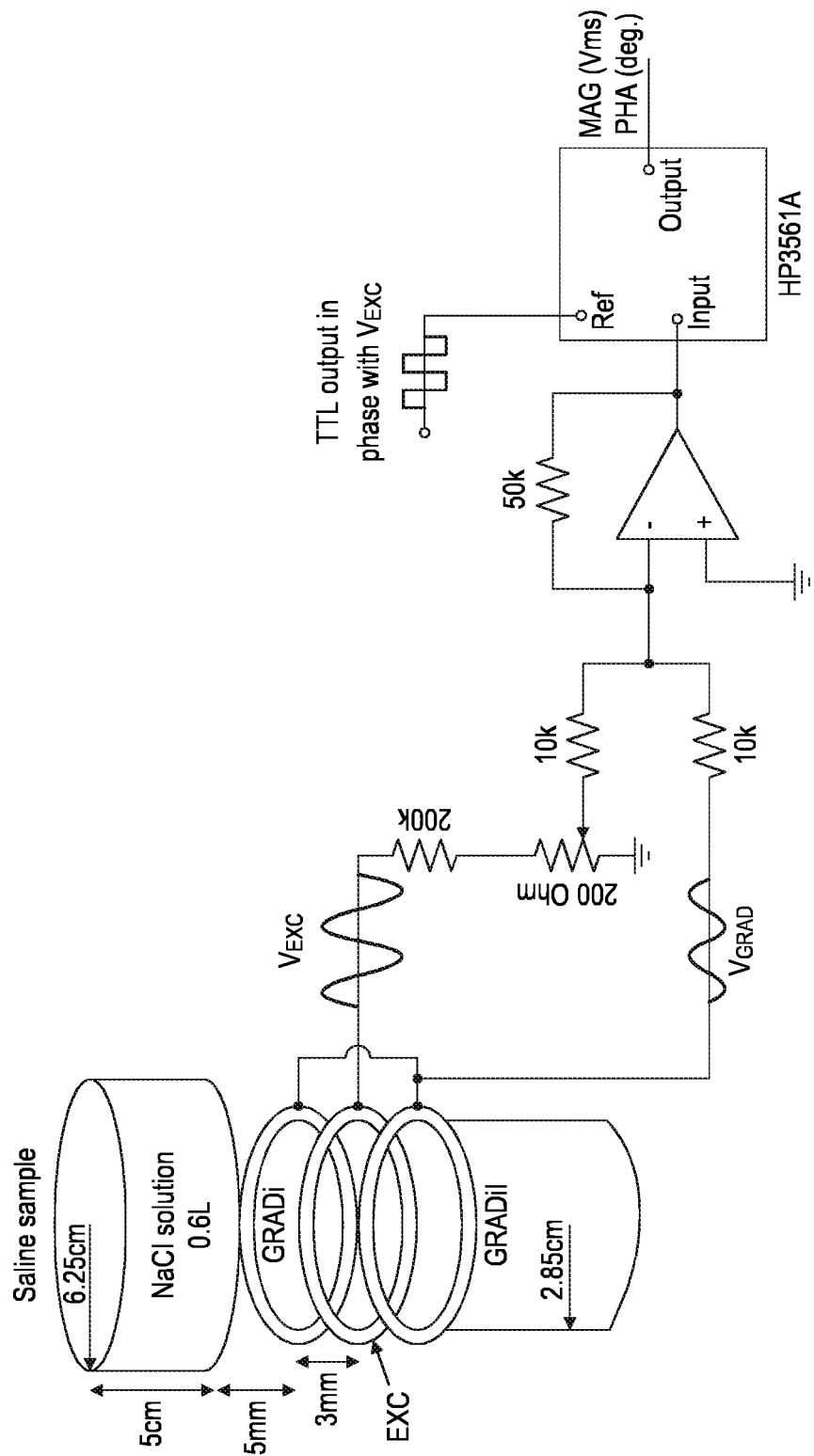
FIGS. 1 and 2 are diagrams of a laboratory prototype apparatus according to one aspect of the invention.

It has been realised that contactless and deeper assessment of the cervix can be achieved using a technique called magnetic impedance spectroscopy (MIS). Magnetic impedance spectroscopy is already known for measuring the properties of the brain and liver tissue (see, for example, IEEE Transactions on Biomedical Engineering Vol 50 2003 07 01, pp 870-880 Scharfetter et al), and has been suggested as a method of quantifying ischaemia, but it has not previously been proposed as a method of measuring the structure, composition and electrical conductivity of cervical or other reproductive tract tissue. There are many practical problems to overcome in order to obtain the required sensitivity and accuracy for the use of MIS in the cervical environment and it is not straightforward to simply adapt the known MIS techniques. In particular, there are difficulties created by the limited working space for an MIS probe in the cervical environment. It is not straightforward to simply adapt known MIS probes for use in the vagina. The Scharfetter apparatus, for example, requires the coils of the apparatus to surround or to be placed on opposite sides of the tissue being measured. This is clearly not practical for measuring the cervix. Known MIS apparatus is also often too large for use in the confined vaginal space which is problematic because of the requirement for the MIS probe to be located in very close proximity to the tissue being measured. Miniaturisation of an MIS probe is challenging because there is a cube relationship between the coil diameter and the detected signal so that even modest reductions in the size of the probe cause a very significant and unwanted drop in sensitivity. Furthermore, it is not obvious how to screen the probe from unwanted sensitivity to the vaginal wall or other adjacent tissue that is not the target tissue whose electrical conductivity it is desired to measure.

The MIS technique is performed using apparatus in the form of an MIS probe which includes a sensor that can measure the conductivity of tissue without the need for surface electrodes being in contact with the tissue (in contrast with EIS techniques which require contact). The probe includes a coil through which an electrical current can be passed and that can be placed close to the cervix. The current produces a magnetic field that induces small currents within the cervical tissue. These small currents, in turn, produce small perturbations in the magnetic field which can be used to determine the electrical conductivity of the tissue.

One possible apparatus design uses a single coil both for inducing currents in the tissue and for detecting the resulting small perturbations in magnetic field. This design can record large changes in conductivity but is subject to significant errors caused by thermal and geometrical drifts that make it unsuitable for use in vivo.

An improved apparatus design which addresses these errors uses one coil to induce current ("excitation means") and at least two further coils connected as a gradiometer to record the perturbations in magnetic field ("detection means"). Thermal and geometrical errors may be reduced by a repetitive displacement of the coil assembly.

Using the principle of electromagnetic reciprocity, it is alternatively possible to use the gradiometer as the excitation means and the excitation coil as the detection means.

In an embodiment of the claimed invention, two sensing coils are placed at equal distances from the excitation coil and the sample is placed in front of one of the sensing coils.

Unlike the prior art MIS systems, the sensing coils and excitation coils are all arranged in a line with the sample tissue at one end thereof. The sample tissue is not located between the coils i.e. the coils do not surround the sample or access it from more than one direction. In Scharfetter, the field is very high close to the excitation coil which is a deterrent to placing the gradiometer close to it (because the gradiometer is likely to pick up a very large unwanted signal from the excitation coil, reducing sensitivity to the relatively small signal from the tissue sample. The unique co-linear arrangement of the present invention means that the probe is able to fit into the confined vaginal space (or other internal space) and access the sample tissue from one direction only.

In use, an alternating electric current flows through the excitation coil and induces the primary magnetic field. The magnetic field thus induces an electric field in the sample which induces electric eddy currents. The eddy currents in the sample then produce the secondary magnetic field. Both the primary and secondary magnetic fields produce an electromotive force (e.m.f.) in the sensing coils. When two sensing coils are connected together in anti-phase, the voltages induced by the primary magnetic field are cancelled out and only the difference from the secondary magnetic field remains. When the sample is placed nearby one of the sensing coils, whilst further away from the other, the e.m.f. in the two sensing coils are different due to the different distances to the sample. A quasi-static approximation of the e.m.f. can be given by equation 1:

$$\frac{\Delta V}{V} = Pf\mu_0(2\pi f\varepsilon_0\varepsilon_r - j\sigma) + Q\chi \qquad (1)$$

where $\Delta V$ is the e.m.f. from the secondary magnetic field, V is the e.m.f. from the primary magnetic field, $\mu_0$ is the permeability in a vacuum, f is the frequency of the drive current, co is the permittivity in a vacuum, $\varepsilon_r$ is the relative permittivity of the sample, a is the electric conductivity of the sample, $\chi$ is the magnetic susceptibility of the sample, P and Q are geometrical factors related to sample size, shape and the distance from the coils The eddy currents in the sample generate both in-phase and quadrature signals $\Delta V$ in the sensing coils, compared with the primary signal V, which are given as the real and imaginary parts in equation (1), respectively. The out-of-phase signal of $\Delta V$ results from the resistive component of the sample and is proportional to the sample conductivity and drive frequency.

Specification

It is desired for the apparatus to have the following specification:

| | |
|---|---|
| Conductivity range to be measured | 0.1 Sm$^{-1}$ to 1.0 Sm$^{-1}$ |
| Frequency range | 50 kHz to 500 kHz |
| Accuracy required | 10% over the range of conductivities |
| Mechanical constraints | less than 30 mm diameter |

Laboratory Prototype Apparatus

A prototype apparatus based upon the gradiometer principle has been constructed and tested in the laboratory. The prototype apparatus uses coils that are larger (57 mm diameter) than will be possible in-vivo. It is known (see: Hart et al., A non-invasive electromagnetic conductivity sensor for biomedical applications, IEEE Trans. on Biomed. Eng., 35, 12, 1011-1021, 1988) that sensitivity will reduce in proportion to $r^3$ (where r is the coil radius) but this reduction can be partially compensated by increasing the number of turns on the current induction coil.

As shown in FIG. 1, the prototype apparatus comprises a coil probe (two gradiometer coils GRADi and GRADii, an excitation coil EXC aligned coaxially, wound on the 57 mm diameter former, an operational amplifier circuit and a dynamic signal analyser ((HP3561A Signal Analyzer, Hewlett-Packard, USA)). The sample (0.6 l NaCl solution) is placed on the top of the coil assembly.

The coils were mounted horizontally and a mechanical jig was constructed to enable saline filled samples with a range of conductivities to be placed in contact with the coil assembly.

Figure 2A:
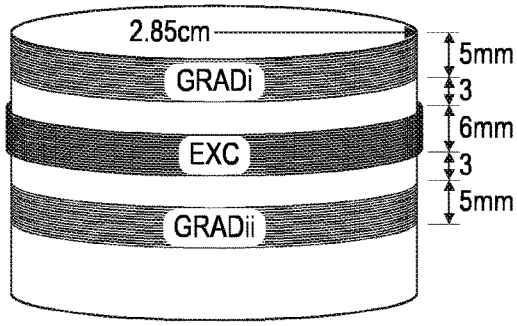
Figure 2B:
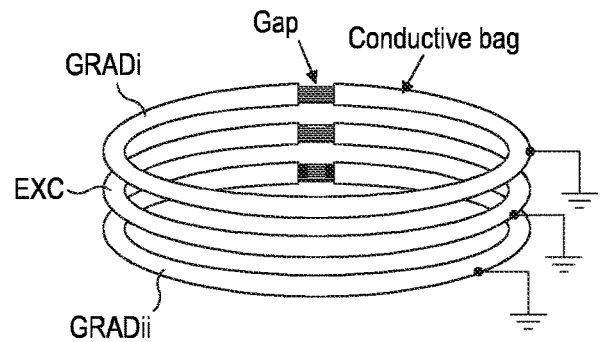

Two gradiometer coils are placed on either side of the excitation coil with a separation of 3 mm (FIG. 2). Referring to FIG. 2 (a), the probe consists of a gradiometer (two coils GRADi and GRADii) and an excitation coil (EXC) placed 3 mm from each gradiometer coil. The three coils are aligned coaxially. (b) Each coil is enclosed with a carbon loaded conductive plastic film (grounded). A gap is left between the beginning and end of the shielding bag in order to avoid any current induced on the film.

Each gradiometer coil (GRADi, GRADii) is made of 20 turns of 0.21 mm diameter wire, shielded with a conductive plastic film (RS 550-117, RS Components Ltd., UK), and wound on a former with 57 mm external diameter. The excitation coil (EXC) uses 26 turns of 0.45 mm diameter wire, shielded with a conductive plastic film, and placed between the two gradiometer coils.

The excitation coil is driven with a 100 kHz, 5.02 $V_{rms}$ sinusoidal signal ($V_{EXC}$) from a function generator. The residual signal from the gradiometer, $V_{GRAD}$, is further reduced by using an operational amplifier circuit. $V_{EXC}$ is connected to a voltage divider that is adjusted to subtract the in-phase residual signal from the gradiometer and leave the 90°-out-of-phase signal resulting from current induced in the saline sample. The output voltage of the amplifier is analysed by the dynamic signal analyzer which gives the signal magnitude ($V_{OUT}$) and phase difference ($\phi$) compared to $V_{EXC}$. The coil parameters and voltages (at 100 kHz) on each coil when no sample is present are given in Table 1 below.

TABLE 1

The coil parameters and voltages (at 100 kHz) across each coil when no sample is present.

| Coil | L (µH) | R(Ω) | Z(Ω) | V⁰ | φ(°) |
|---|---|---|---|---|---|
| EXC | 73.05 | 0.935 | 45.9 | 5.02 $V_{rms}$ | 0 |
| GRADi | 47.85 | 1.865 | 30.12 | 1.430 $mV_{rms}$ | 0.7 |
| GRADii | 48.15 | 2.09 | 30.34 | 1.429 $mV_{rms}$ | 0.5 |
| GRADi + ii | | | | 194.6 $µV_{rms}$ | −67.7 |

L=induction, R=resistance, Z=impedance at 100 kHz. V⁰ is the voltage across each coil and φ is the phase difference compared with the voltage on the EXC.

Laboratory Measurements

Five saline samples were made with conductivities of 0.0003, 0.235, 0.520, 0.743 and 1.016 S·m⁻¹, at room temperature of 21.5±1° C. The conductivities were measured using a conductivity meter (Model Jenway 470, Bibby Scientific Limited, UK). The solutions were placed in five plastic containers (round, 0.6 L capacity, 12.5 cm diameter, 5 cm high).

Measurements were made by placing each sample on the top of the probe and monitoring the magnitude and phase signal from the output of the HP3561A every second continuously for 1 minute. Two 1-minute baseline measurements were taken immediately before and after the sample measurement in order to minimise any background signal drift. The monitored data from each measurement were then averaged by the dynamic signal analyzer. Each measurement was repeated 10 times for each sample.

The sample conductivity n is proportional to the imaginary part of the output voltage change $\Delta\text{Im}[V_{OUT}(\sigma)]$ which is given by:

$$\Delta\text{Im}[V_{OUT}(\sigma)]=V_{OUT}^s \times \sin(\phi_s) - V_{OUT}^0 \times \sin(\phi_0)$$

where $V^s_{OUT}$ and $\phi_s$ are the output magnitude and phase signal when the sample is present, while $V^0_{OUT}$ and $\phi_0$ are the averaged output magnitude and phase signal from those two baseline measurements taken immediately before and after the sample measurement.

Laboratory Results

Figure 3:
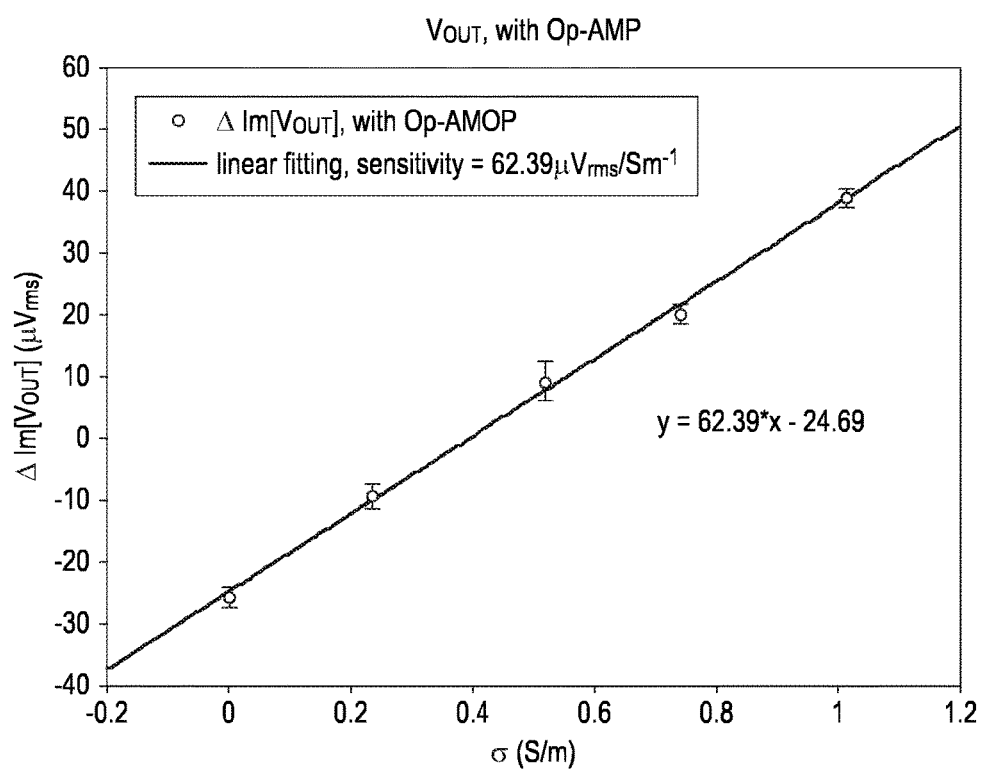
FIG. 3 shows results from the laboratory prototype apparatus.

FIG. 3 shows the results from the measurements on the five saline samples. The imaginary part of the voltage change is plotted versus the conductivity (a), and fitted with a linear curve. The sensitivity of the output signal to the saline conductivity is 62.39 $\mu V_{rms}/Sm^{-1}$. The data point and error bars for each conductivity show the mean and standard deviation of the 10 measurements for each saline sample. These results are consistent with a theoretical analysis that has been carried out The results given in FIG. 3 demonstrate 'proof of principle' of the gradiometer technique in that the output is proportional to the conductivity of the saline. The mean of the standard deviations on the measurements is about 2 µV which corresponds to 0.032 $Sm^{-1}$. This represents a percentage error of 10% on a conductivity of 0.32 $Sm^{-1}$, which is a typical conductivity for cervical tissue. This meets the desired design specification. However, when the coil sizes are reduced to a size suitable for use in vivo (e.g. at the cervix) the noise performance will be worse by at least a factor of two.

In-Vivo Apparatus

In order to increase the signal-to-noise-ratio (SNR) further it is necessary to increase the magnetic field produced by the drive coil. This could be achieved by using a higher coil inductance and a higher drive voltage. Alternatively, a novel approach could be used in which the drive coil could be operated in a series resonant circuit. This will enable a low drive voltage to achieve a high voltage across a high inductance coil. This technique would normally give rise to errors because of variations in the Q of the resonant circuit. However, it has been found that a small search coil can be used to measure the magnetic field produced by the drive coil and this measurement can be used for demodulation and correction of the gradiometer output.

A second novel approach is to use magnetically soft ferrite or other materials with a high magnetic permeability, as a core for the coils. This enables the size of the coil assembly to be reduced considerably whilst maintaining the SNR. Use of concentric ferrite mouldings also increases sensitivity in front of the face at the target tissue whilst reducing sensitivity to adjacent non-target tissues.

One or both of the above approaches enable an in-vivo probe apparatus with adequate SNR to be produced, without the need to repetitively displace the coil assembly as mentioned above. In addition, by selecting the material that will be used for the coil former to have a low coefficient of thermal expansion and by potting of the coils in the in-vivo sensor in order to minimise geometrical changes the SNR can be increased further.

The design of a phase sensitive measurement system implemented using a Field Programmable Gate Array (FPGA) offers a further improvement in performance, reducing phase errors in the measurement.

The accuracy of cervical measurements using the air-cored transducer of the laboratory prototype described above would be adversely affected by the vaginal wall in the cervical environment. The second novel approach mentioned above, using a ferrite sleeve within which the coils are wound, tackles the effect of the vaginal wall so giving more accurate results. Using a ferrite core, the following results were achieved:

- The system has been calibrated over the conductivity range $0.01\ Sm^{-1}$ to $1.0\ Sm^{-1}$.
- The system has been used to make calibrated measurements with a good signal-to-noise ratio at 50 kHz, 100 kHz and 300 kHz.
- The reproducibility of the measurements, in terms of the standard deviation as a fraction of the mean, is less than 5% at all three frequencies for a conductivity of $0.5\ Sm^{-1}$. It is expected to see conductivities similar to this for the soft tissue of the cervix.
- The diameter of the ferrite-core probe made of ferrite rod is achieved at 25.9 mm, below 30 mm.

In-vivo apparatus has been designed in the form of a new prototype gradiometer system, compatible in size with the human vagina. The system hardware includes a ferrite-cored probe, electronic circuitry for amplifying the current input and voltage output signals, and a control and analysis programme written in LabView software (v2012, National Instruments Corp., USA).

Figure 4:
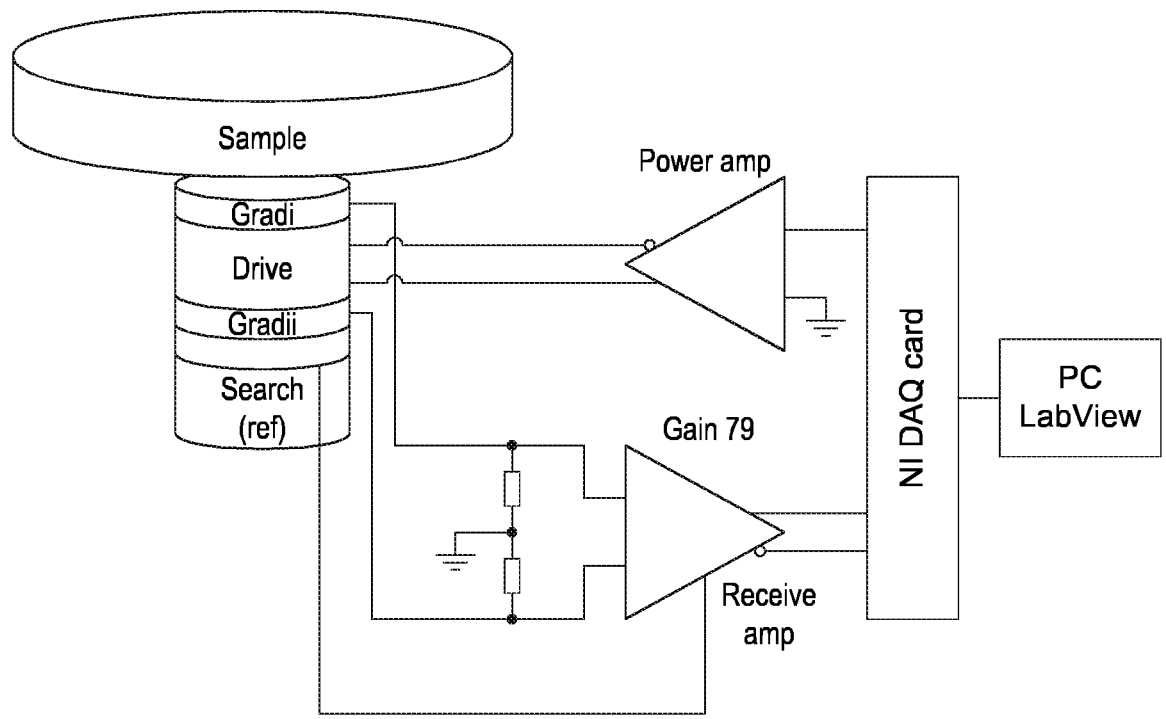
FIG. 4 is a diagram of an air-cored gradiometer apparatus.
Figure 5:
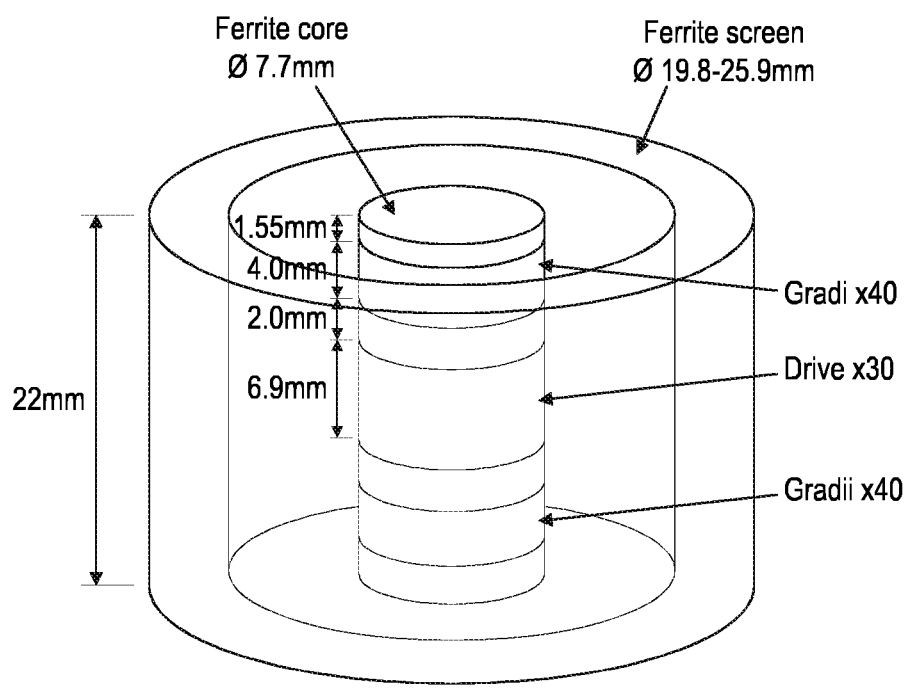
FIG. 5 is a diagram of a ferrite-core gradiometer apparatus.

FIG. 4 shows apparatus using the air-cored probe while FIG. 5 shows a ferrite-core probe on which a drive coil (30 turns, copper wire thickness 0.2 mm) and two gradiometer sensing coils (40 turns each, copper wire thickness 0.1 mm) are wound on the central rod. The two sensing coils are equidistant from the drive coil to form a gradiometer system. The drive signal, controlled by the LabView programme via a digital-to-analogue converter interface, is amplified by a power amplifier. The output from the differential amplifier is connected to an A/D converter (DAQ, NI USB-6366, National Instruments Corp. USA) and analysed by the programme.

Sensitivity Measurements Using Saline Solutions:

Distilled water and four different concentrations of saline solution (electrical conductivity ranges between $0.1\ Sm^{-1}$ to $1.1\ Sm^{-1}$) were used to fill 0.6 L plastic pots and placed on the top of the probe. The gradiometer signals related to the sample electrical conductivity from the five solutions are given in Table 2. Ten measurements were taken for each sample with the baseline signal, when no sample was placed on the probe, subtracted. The mean value and standard deviations were calculated from the sets of ten measurements. The ratios of the standard deviation to the mean value are less than 13% for saline solutions. The gradiometer signals related to the saline sensitivity in Table 2 are also plotted against saline conductivities shown in FIG. 6.

Figure 6:
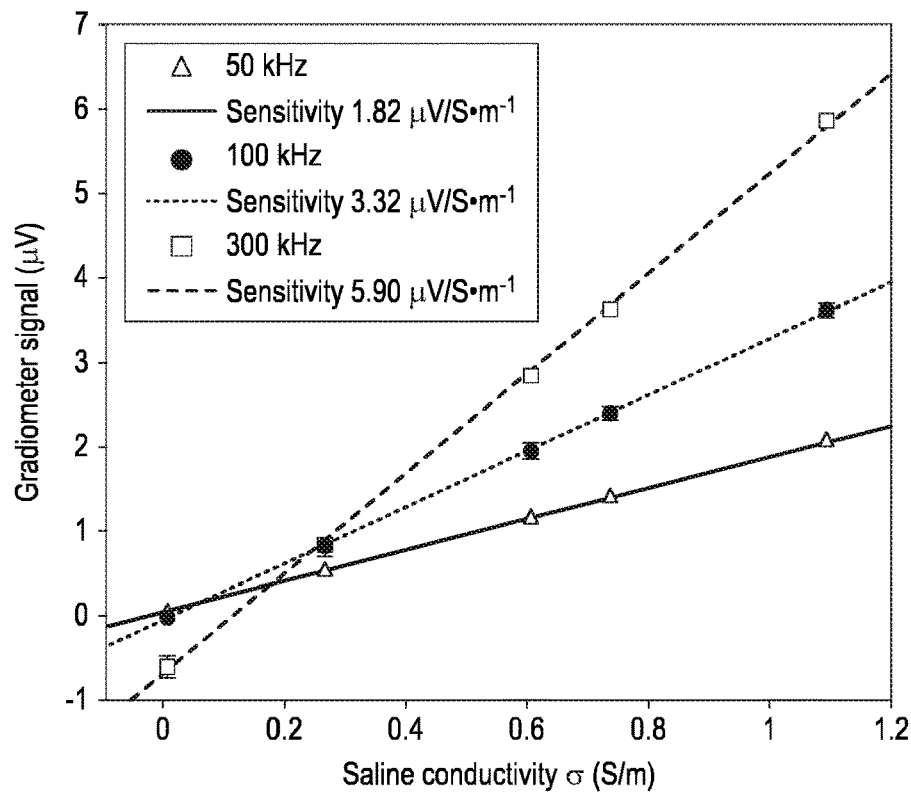
FIG. 6 shows gradiometer signal versus saline conductivities.

The gradiometer signal is shown in FIG. 6 at frequencies 50 kHz, 100 kHz and 300 kHz and plotted against the saline conductivity and fitted with linear curves. Saline should have a conductivity which is independent of frequency and hence a linear relationship is expected. The slope of those linear curves give the signal sensitivity at each frequency, and these linear relations are used for calculating the conductivity of the sample. When applied to human tissue the conductivity should increase with increasing frequency.

TABLE 2

The gradiometer signal (Grad. Signal) related to the saline conductivity at different frequencies. The mean value and standard deviation (Stdv.) calculated for the 10 measurements are plotted in FIG. 6. The ratios of the standard deviation to the gradiometer signal are less than 13% for saline solutions.

| saline conductivity σ (S/m) | 50 kHz | | | 100 kHz | | | 300 kHz | | |
| --- | --- | --- | --- | --- | --- | --- | --- | --- | --- |
| | Grad. Signal (μV) | Stdv. (μV) | Stdv./Grad. (%) | Grad. Signal (μV) | Stdv. (μV) | Stdv./Grad. (%) | Grad. Signal (μV) | Stdv. (μV) | Stdv./Grad. (%) |
| 0.0003 | 0.047 | 0.050 | 107.3 | −0.013 | 0.078 | 584.9 | 0.603 | 0.121 | 20.14 |
| 0.266 | 0.514 | 0.025 | 4.85 | 0.795 | 0.103 | 12.96 | 0.817 | 0.085 | 10.43 |
| 0.606 | 1.129 | 0.038 | 3.35 | 1.959 | 0.085 | 4.34 | 2.823 | 0.083 | 2.93 |
| 0.739 | 1.377 | 0.024 | 1.73 | 2.372 | 0.060 | 2.51 | 3.612 | 0.087 | 2.42 |
| 1.098 | 2.043 | 0.030 | 1.46 | 3.617 | 0.053 | 1.47 | 5.869 | 0.047 | 0.81 |

FIG. 6 shows sensitivity test results when using distilled water and saline samples. A linear fit is shown for the results. The signal sensitivities to the saline conductivity are 1.82 µV at 50 kHz, 3.32 µV at 100 kHz, and 5.90 µV at 300 kHz. Sensitivity rises with frequency as expected but the relationship is not a simple one as it depends upon the various filters applied in the measurement system. The drive voltage was fixed at 1 Vpp.

Sensitivity Versus Distance

Measurements have also been performed on a 1 $Sm^{-1}$ saline sample, with different spacing between the probe and the sample (2.5 mm to 11.5 mm) at 100 kHz. The dimension of the saline sample is compatible to human cervix (6.51 cm in diameter, 3.0 cm in length). The results are shown in Table 3 and plotted in FIG. 7; the mean values and the standard deviations for each data point were taken from 10 repeated measurements. As expected, signal sensitivity falls with increasing distance from the gradiometer.

TABLE 3

The gradiometer signal (Grad. Signal) related to the saline conductivity at different distance from the probe. The mean value and standard deviation (Stdv.) calculated for 10 measurements are plotted in FIG. 7.

| distance (mm) | Grad. Signal (µV) | Stdv. | ratio (%) |
|---|---|---|---|
| 2.5 | 4.872 | 0.042 | 0.86 |
| 3.5 | 3.564 | 0.036 | 1.01 |
| 4.5 | 2.746 | 0.045 | 1.63 |
| 5.5 | 2.148 | 0.044 | 2.07 |
| 6.5 | 1.666 | 0.029 | 1.73 |
| 7.5 | 1.315 | 0.025 | 1.90 |
| 8.5 | 1.082 | 0.041 | 3.81 |
| 9.5 | 0.886 | 0.037 | 4.13 |
| 10.5 | 0.730 | 0.030 | 4.09 |
| 11.5 | 0.606 | 0.032 | 5.27 |

The ratios of the standard deviation to the gradiometer signal are less than 5% for the distance up to 10 mm.

In the laboratory prototype, a thin layer of ferrite sheet (0.5 mm thickness) is used as the magnetic screen between the air-cored probe and vagina wall, which shielded out 70% of the vaginal wall signal.

The in vivo apparatus using a ferrite-cored probe with thicker ferrite screening and smaller diameter, will shield out more than 90% of the vagina wall signal, and the remaining signal from the vagina wall is less than 10% of the signal from cervix.

MIS technology could well prove applicable to other areas of birth management including the prediction of the success of artificial initiation of labour and the successful diagnosis of cervical insufficiency, a recognised condition not amenable to prospective diagnosis, currently only presumed when a pregnancy has failed in mid-trimester or thereafter.

Probes for In Vivo Measurements
Apparatus and Methods
Coil System

Two types of MIS gradiometer coil have been tested. The first uses a Borosilicate glass former and is effectively air cored and the second uses a ferrite rod with an outer cylindrical ferrite shield. It will be understood that other non-ferritic materials would also be suitable for the tube. Each MIS gradiometer consists of an excitation coil and two sensing coils wound coaxially on a glass former. An alternating source is connected to the excitation coil and the primary magnetic field is induced in proportion to the applied current. For the air-cored MIS gradiometer, 60 turns were used on the excitation coil and 40 turns on the sensing coils which were wound tightly on a glass tube with an outer diameter of 30.0 mm and inner diameter of 26.0 mm. The spacing between each sensing coil and the excitation coil was 0.5 mm.

Figure 8:
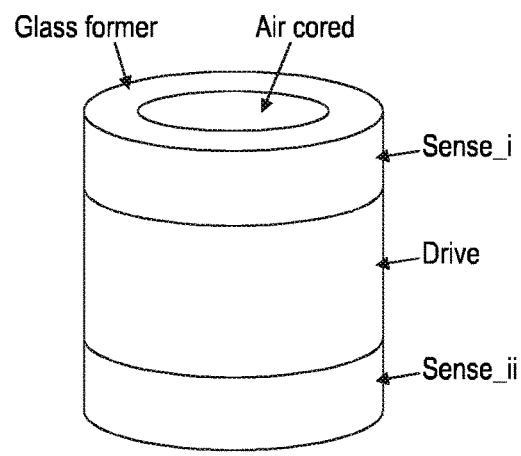
FIG. 8 shows air-cored and ferrite-cored coil systems with lengths and diameters given in mm.
Figure 8:
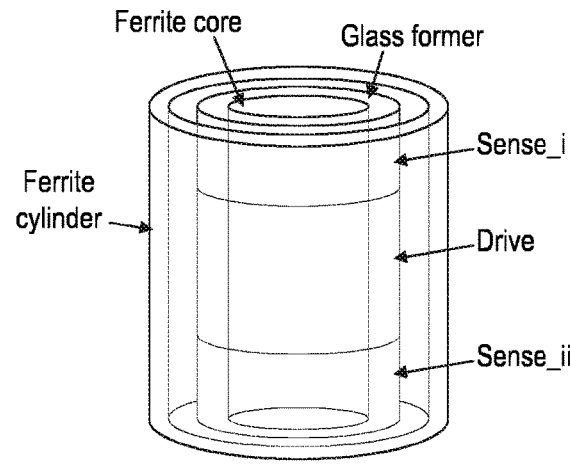
Figure 8:
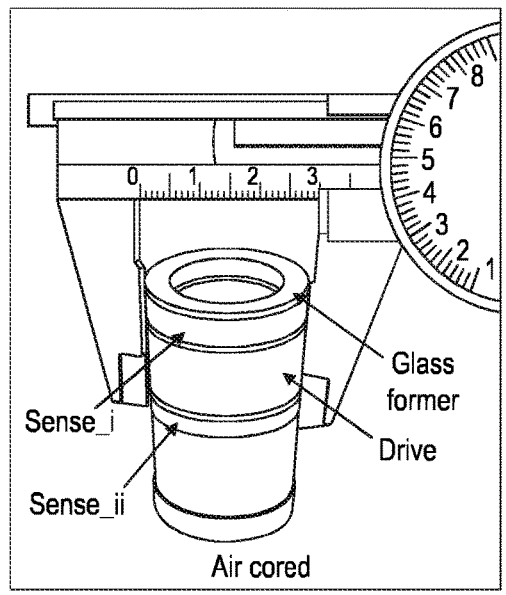
Figure 8:
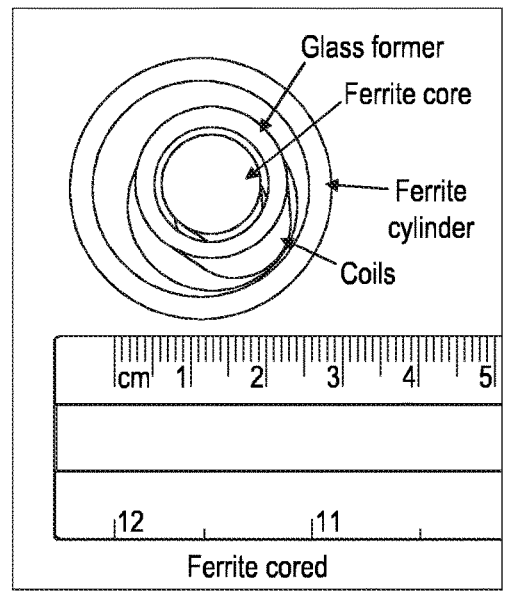

For the ferrite-cored MIS gradiometer, 30 turns were used on the excitation coil and 40 turns on the sensing coils which were wound on a glass former of 15.0 mm in outer diameter. A commercially available ferrite rod with diameter of 9.8 mm was placed inside the glass former and both were placed within a ferrite cylinder of 26.0 mm diameter. Both MIS gradiometers were made the same length (22.0 mm) as shown in FIG. 8.

Hardware

The drive coil was connected to a power amplifier whose input signal was controlled by a PC via a digital-to-analog interface (NI DAQ 6366, National Instruments). The drive and receive signals were controlled and processed by a computer program (NI LabView 2012) installed on the PC and interfaced with a digital-to-analog converter (NI-USB 6366). The drive signal operated at a sample rate of 2 M samples per second and with a DAQ resolution of 16 bits. Three excitation frequencies, 50 kHz, 100 kHz, and 300 kHz, were controlled by the PC, with an output amplitude of 20.0 Vpp and resulting drive currents of 0.57 A, A, and 0.10 A, respectively. The PC controller used commercial software (LabView 2012, National Instruments). The receiver signal from the sensing coils was connected to a differential amplifier where any unbalanced signal was subtracted in order to optimize the signal from the sample. The block diagram of the MIS gradiometer system using the air-cored probe is shown in FIG. 4. It will be understood that the air-cored probe shown in the block diagram in FIG. 4 can be replaced with the ferrite-cored probe shown in figure in the ferrite-cored system.

Electric-Field Shielding

Figure 9:
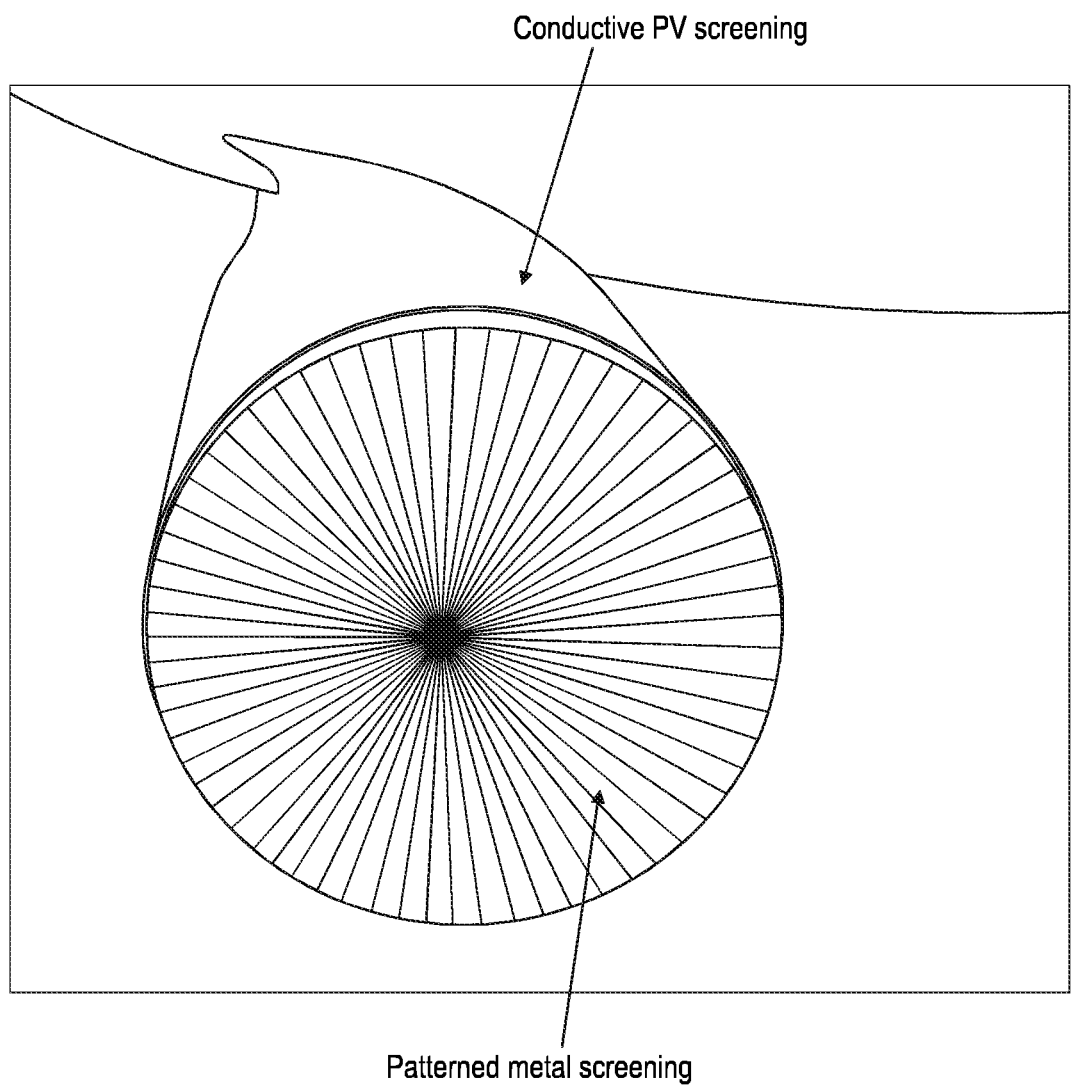
FIG. 9 shows the patterned electric-field screening for the MIS system.

Two types of the electric-field shielding have been tested. The first used commercially available conductive PV film (Black Conductive ESD-Safe Bag, RS Components Ltd., UK) and completely covered the whole probe and earth ground. The second type used two thin aluminised polyester films which covered the probe, while on the probe face it was patterned in petals to minimise unwanted eddy currents. A conductive PV film was also used to cover the sides and the top of the aluminised films and a gap was left to prevent eddy currents as shown in FIG. 9.

Simulations

Simulation used the Finite Element Method implemented using commercially available software (4.3b COMSOL Multiphysics). Both the induced current in the sample and the gradiometer sensitivity were simulated for both types of MIS gradiometer. 2D and 3D axial-symmetric simulation results of magnetic flux density and induced current density were plotted as a longitudinal cylindrical section as shown in FIG. 10. In FIG. 10(*a*) air-cored probe and (b) ferrite-cored probe, the 2D magnetic scalar flux density is plotted as a colour scale and the vector direction plotted as an arrow field from r=0 mm to r=40 mm with the rotational axis at r=0. The magnetic field was confined by the geometry of the ferrites for the ferrite-cored system in FIG. 10(*b*), unlike the air-cored system where the coils are surrounded by magnetic flux. The 2D induced current density in saline samples simulated for both coil systems are shown in FIGS. 10(*c*) and (*d*). For the air-cored system in figure the induced current density is higher in the surrounding saline than in the saline near the probe face where the saline is further away from the drive coil. For the ferrite-cored system in FIG.

Figures 10A, 10B:
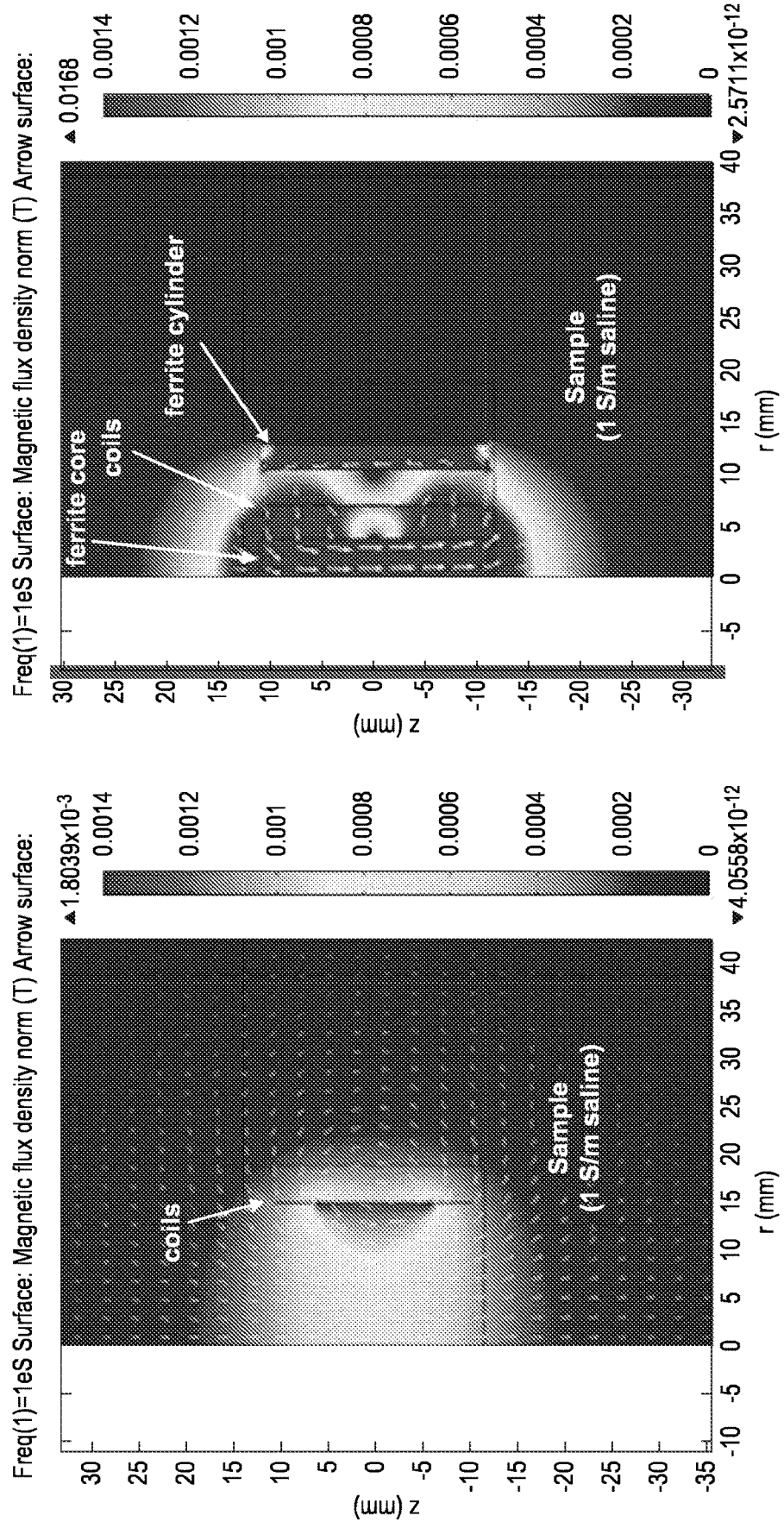
FIG. 10(a) shows simulation results for the axial-symmetric 2D magnetic flux density for the air-cored MIS gradiometer, with small distributed arrows representing the distribution of the magnetic flux.
FIG. 10(b) shows simulation results for the axial-symmetric 2D magnetic flux density for the ferrite-cored MIS gradiometer, with small distributed arrows representing the distribution of the magnetic flux.
Figures 10C, 10D:
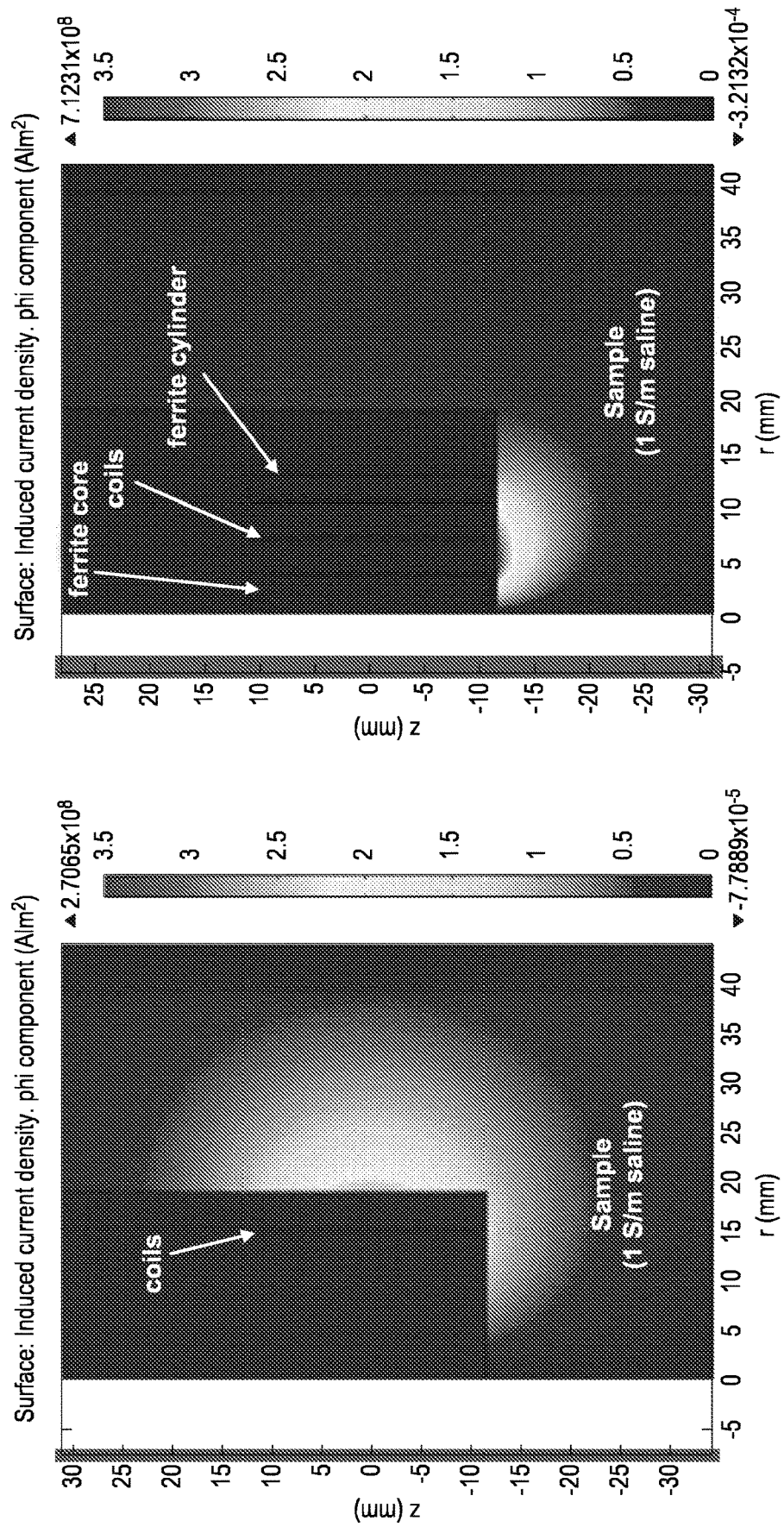
FIG. 10(c) shows simulation results for the 2D inducted current density in saline samples simulated for an air-cored MIS gradiometer.
FIG. 10(d) shows simulation results for the 2D inducted current density in saline samples simulated for a ferrite-cored MIS gradiometer.
Figure 10E:
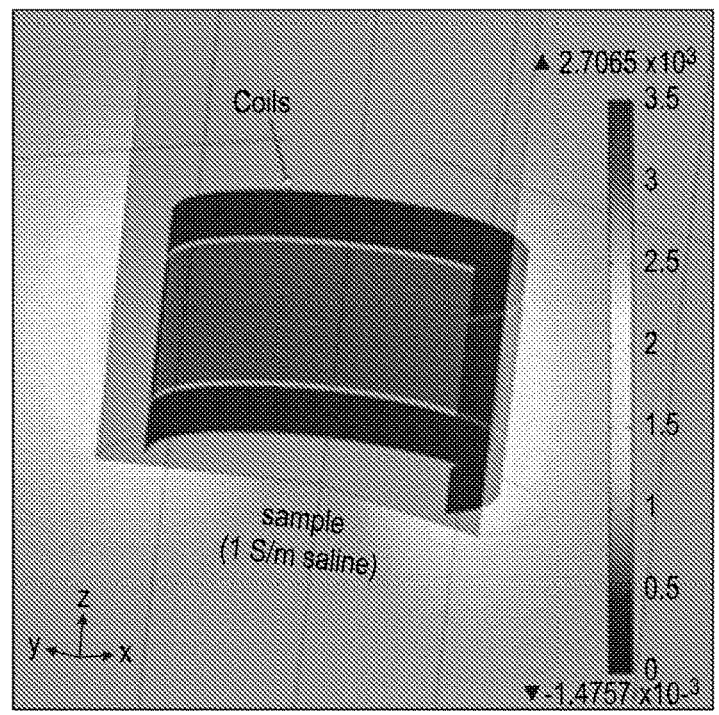
FIG. 10(e) shows simulation results for the 3D induced current density in saline sample for an air-cored MIS gradiometer.
Figure 10F:
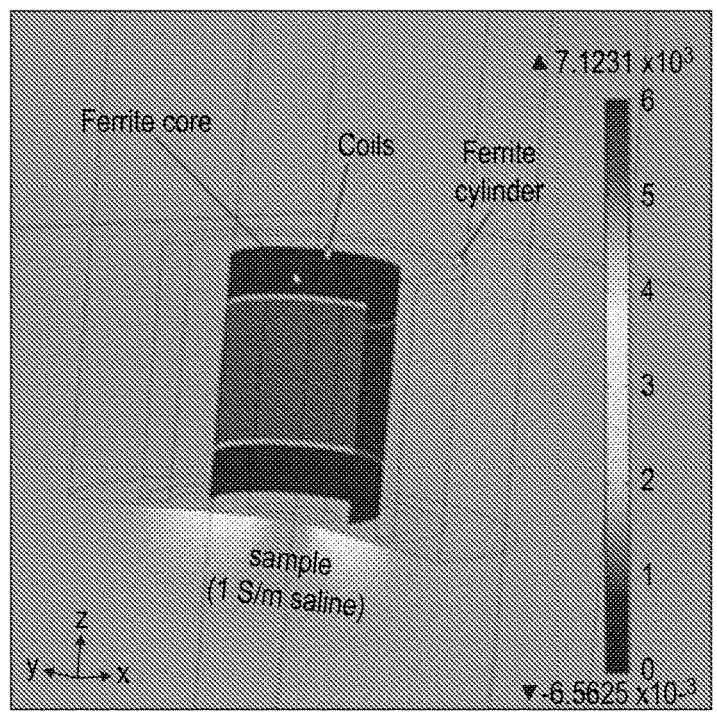
FIG. 10(f) shows simulation results for the 3D induced current density in saline sample for a ferrite-cored MIS gradiometer.

10(d), the induced current density distributes near the probe face similar to the coil radius and is confined by the probe geometry. The 3D induced current density in the saline sample for the air-cored systems is shown in FIG. 10(e) and for the ferrite-cored system in FIG. 10(f). The results are plotted as for FIGS. 10(c) and (d) but in 3D.

Figure 11A:
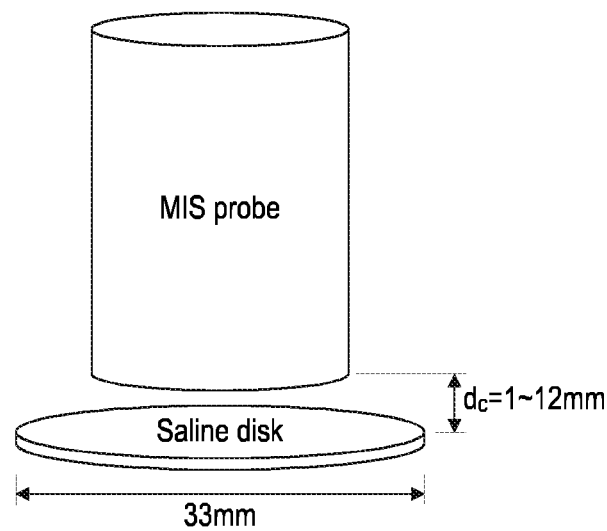
FIG. 11 (a) is a schematic diagram for the signal penetration simulation.
FIG. 11(b) shows simulation results for signal penetration depth.
Figure 11B:
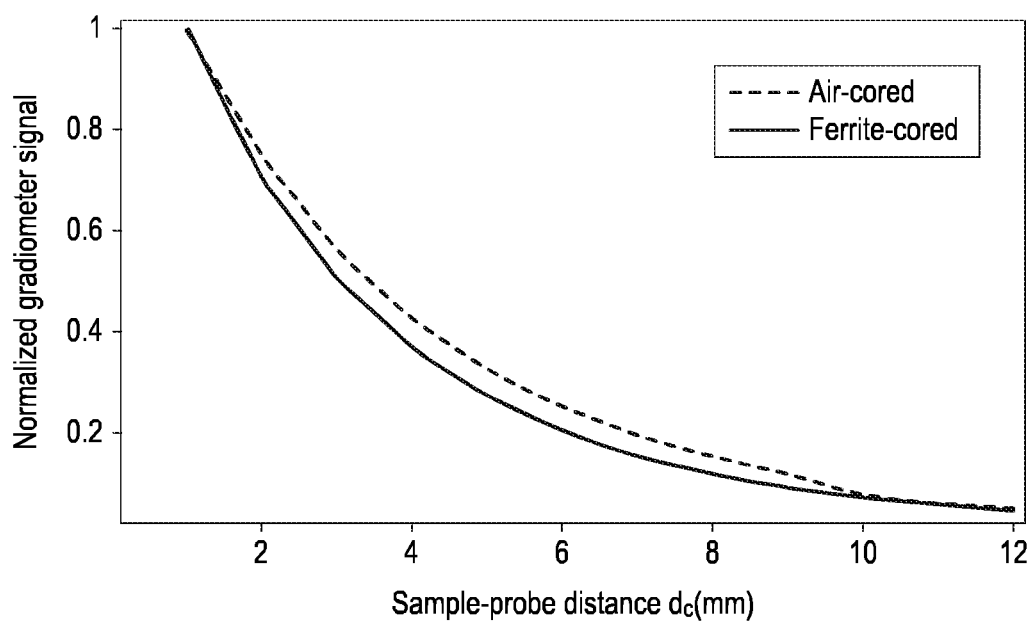

Simulation results for signal penetration depth are shown in FIG. 11(b). A saline disk with 1 mm thickness and 33 mm diameter was moving away from the probe with the distance dc from 1 mm to 12 mm as shown in FIG. 11(a). Gradiometer signal was normalized by the signal when the disk was placed at dc=1 mm. Results from both air-cored and ferrite-cored probe are shown in (b) where the ferrite-cored signal decreased more rapidly than the air-cored signal. Both normalized gradiometer signals decreased to about 50% when the sample-probe distance increased by 2 mm and to less than 10% when the sample-probe distance was more than 10 mm.

Measurements

Measurements with Saline Solutions

Impedance measurements at the three frequencies (50 kHz, 100 kHz, and 300 kHz) were made using samples consisting of distilled water and four sodium chloride solutions, with conductivities within the range of 0.01 $Sm^{-1}$ to 1.3 $Sm^{-1}$. The conductivities of distilled water and saline samples were measured using a commercial conductivity meter (Model Jenway 470, Bibby Scientific Limited, UK). The samples were placed in a 0.6 L round plastic container and placed on top of each MIS gradiometer. The base of the plastic container was of thickness 2 mm. All measurements were performed at room temperature of 20.0° C. to 22.0° C., with a variance of less than 1.0° C. during each measurement. Measurements were taken ten times for each sample. The effectiveness of the electric-field screening was determined by measuring the offset resulting from the measurements made on the distilled water and the saline solutions.

Magnetic Shielding for Surrounding

The objective was to construct gradiometers that would be sensitive to tissue placed in front of the transducer but insensitive to any surrounding tissue. This is particularly important for the proposed in-vivo measurements within the vagina. To determine the magnetic screening effectiveness, both air- and ferrite-cored MIS gradiometers 102 were inserted into a cylindrical container 100 with an inner hollow tube 104 which had an outer diameter $D_2$ of 37.0 mm. The inner tube 104 was connected to a flange 106 which contacted the rim of the container 100 when the inner tube 104 and probe 102 were inserted into the container. This ensured consistent placement of the probe within the container.

Figure 12:
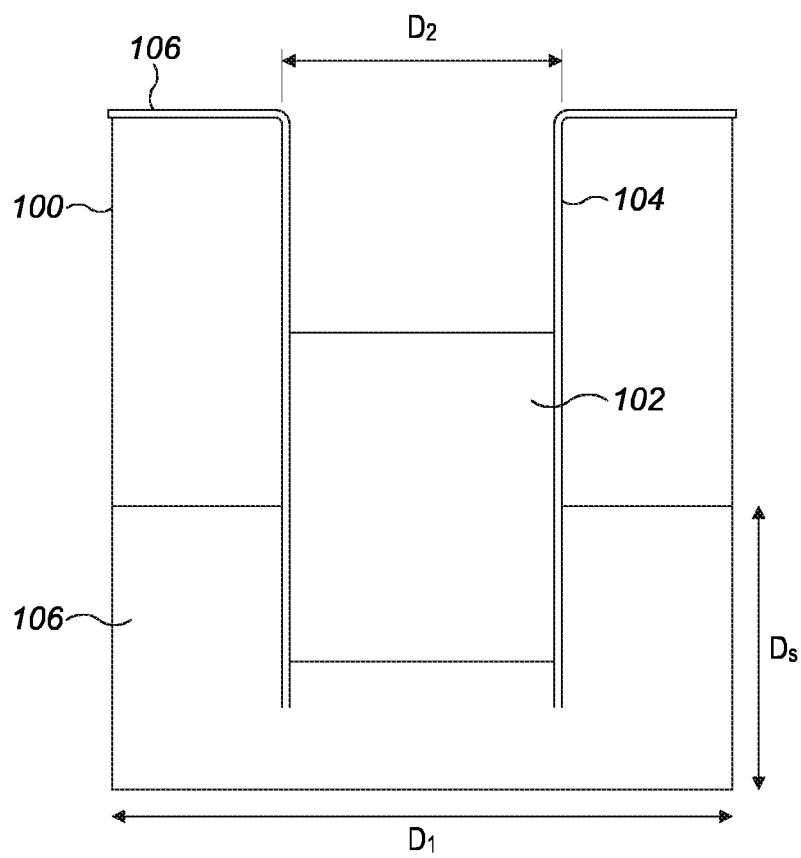
FIG. 12 shows a cylindrical container used to test the effectiveness of the magnetic screening.

The plastic container 100, with inner diameter $D_1$ of 60.0 mm, was filled with 1.1 Sm-1 saline and conductivity measurements were taken at a frequency of 100 kHz and at room temperature. Measurements were made by filling the cylinder with different depths $D_s$ of saline 106 as shown in FIG. 12.

Sensitivity Measurements Versus Sample Distance

A 1.02 $Sm^{-1}$ saline sample was placed in a 0.6 L plastic round container with 12.0 cm inner diameter and 5 cm height. Measurements were taken by increasing the distance between the sample and the probe from 2.5 mm to 55.1 mm for the air-cored probe, and from 2.5 mm to 12.0 mm for the ferrite-cored probe. At each distance measurements were repeated times and all the measurements were taken at room temperature with the drive frequency 100 kHz.

In-Vivo Measurements on Human Forearm

To confirm that the probes are suitable for measuring conductivity in vivo, conductivity measurements were performed on a human forearm at frequencies of 50 kHz, 100 kHz, and 300 kHz. A spacing of 2.5 mm was left between both MIS gradiometers and the forearm. Measurements were taken ten times for each frequency and each measurement was taken for ten seconds.

Results

Conductivity Measurements with Saline Solutions

Figure 13A:
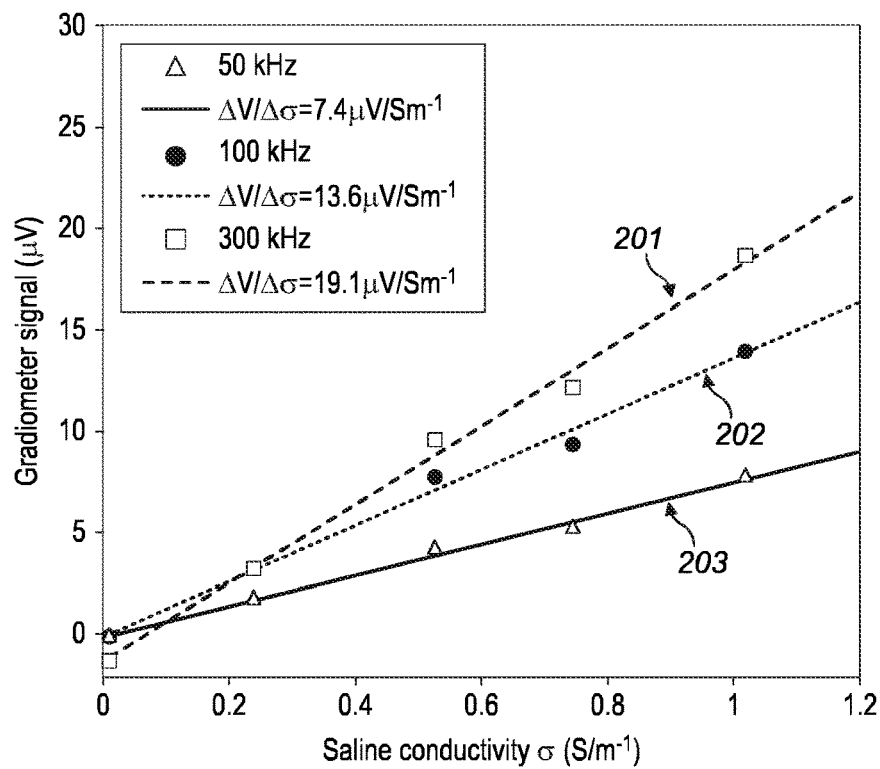
FIG. 13(a) shows results from the conductivity measurements using distilled water and four saline samples at frequencies of 50 kHz (line 203), 100 kHz (line 202), and 300 kHz (line 201) for an air-cored probe.
Figure 13B:
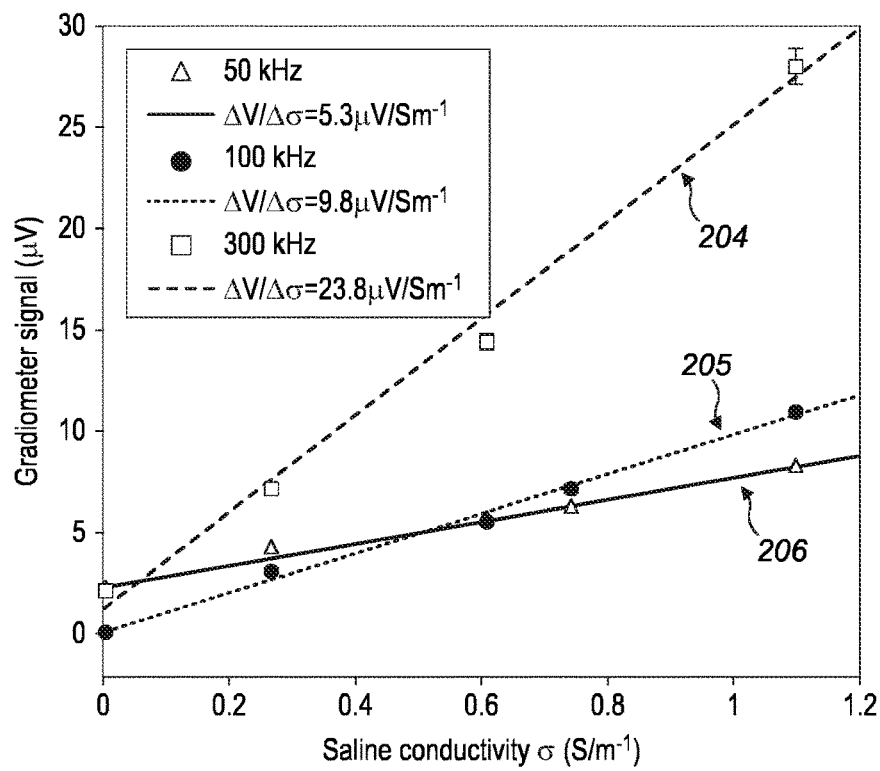
FIG. 13(b) shows results from the conductivity measurements using distilled water and four saline samples at frequencies of 50 kHz (line 206), 100 kHz (line 205), and 300 kHz (line 204) for a ferrite-cored probe.

Conductivity measurements on distilled water and four saline solutions were made with the air-cored and ferrite-cored MIS gradiometers at frequencies of 50 kHz, 100 kHz, and 300 kHz. Ten measurements were taken for each sample at each frequency. FIGS. 13(a) and (b) show the results using air-core and ferrite-cored MIS gradiometers, respectively. The gradiometer output signals are plotted against the conductivity of the samples and a linear curve was fitted to each drive frequency with five data points in each case. Signal sensitivity, defined as the slope of the fitted linear curve, varies with frequency.

Magnetic Shielding for Surroundings

Figures 14A, 14B:
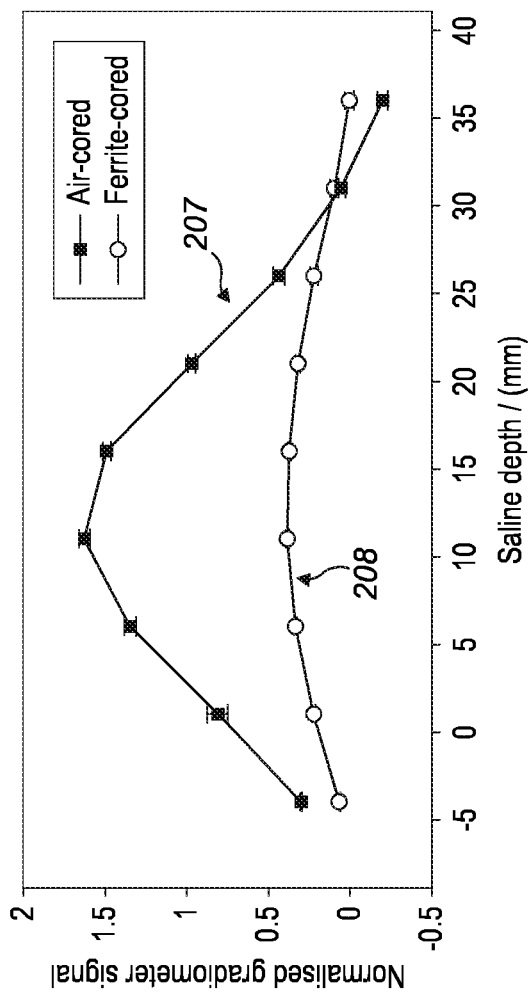

The two MIS gradiometer types were inserted into a 1.0 $Sm^{-1}$ saline cylinder filled to increasing depths. The gradiometer signals, normalized by the signal from a 0.6 L saline pot placed in front of the probe with spacing of 2.5 mm, were plotted against the depth of the saline at a frequency of 100 kHz as shown in FIG. 14a. It can be seen that the maximum sensitivity to surrounding saline occurs when the saline surrounds half of the gradiometer. It can also be seen that the ferrite-cored gradiometer is less sensitive than the air cored gradiometer to the surrounding saline. The maximum contribution from the surrounding saline, i.e. when the saline was filled up to half length of the probe, were also compared with the simulation results as shown in FIG. 14b. The combination of a ferrite core and ferrite screen has the highest magnetic shielding effectiveness compared with either the air cored or unscreened ferrite probes.

Sensitivity Measurements Versus Sample Distance

Figure 15:
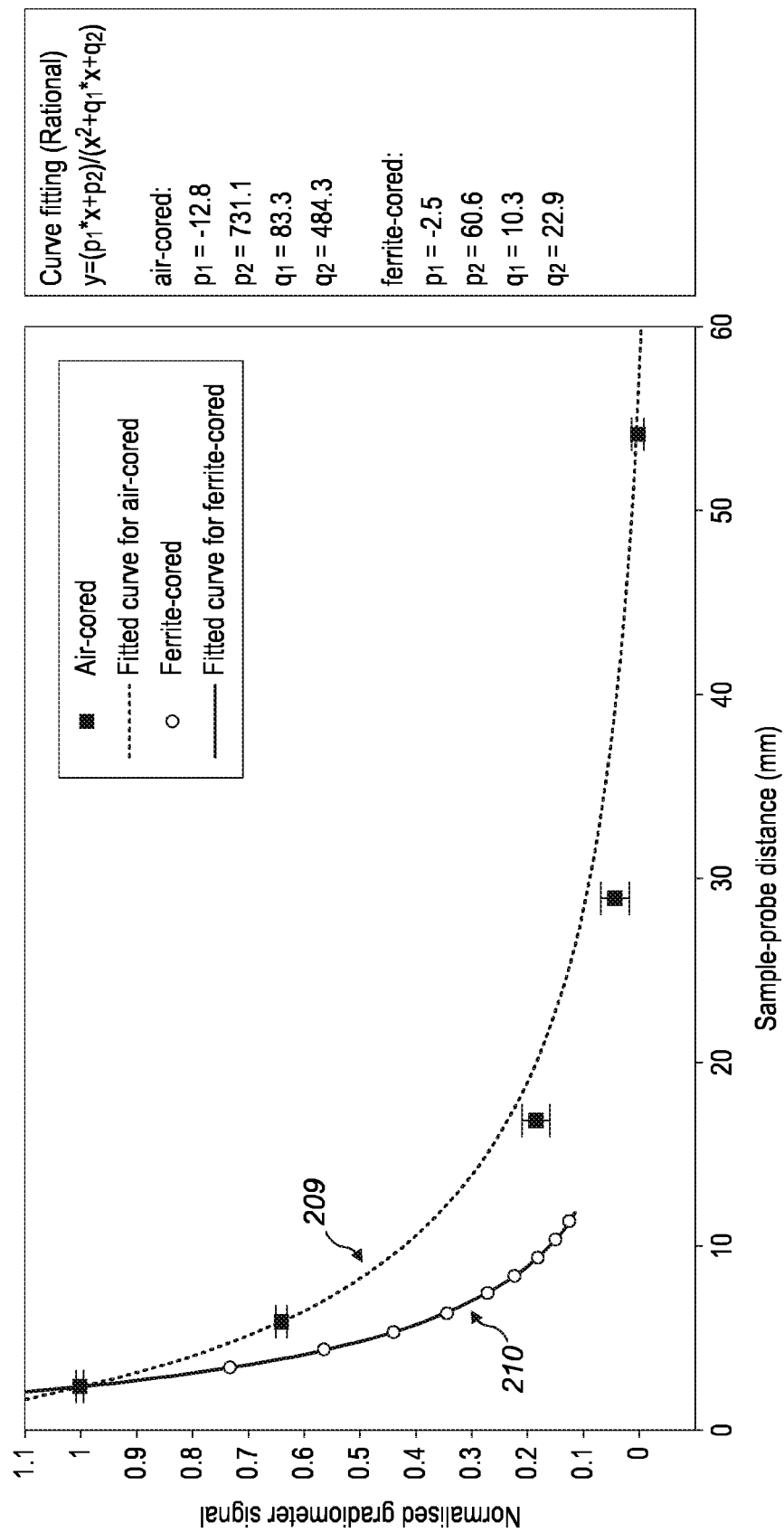
FIG. 15 shows results from sensitivity measurements against sample distance for the air-cored (line 209) and ferrite-cored (line 210) MIS probes.

Conductivity measurements were performed on a 0.6 L and 1.02 $Sm^{-1}$ saline samples (12.0 cm diameter and 5.0 cm in height) with various spacings between the probe and the sample. The gradiometer signal related to the sample conductivity was normalized by the signal when the sample was placed at a distance of 2.5 mm. The measurements were taken with a spacing of 2.5 mm up to 55 mm for air-cored probe, and 2.5 mm up to 12.0 mm for the ferrite-cored probe as shown in FIG. 15. A rational polynomial curve, with the degree of one in the numerator and degree of two in the denominator, was fitted to each data set using the curve fitting tool (MatLab 2014b, The Mathworks Inc., USA), the fitting equation and coefficients were also listed. From the curve fitting results, the signal fell approximately as a square law with distance where the coefficient $p_2$ dominated. The ferrite-cored signal decreased more rapidly than the air-cored signal, which was expected from the simulation results (see FIG. 11).

Conductivity Measurements on Human Forearm

Figure 16A:
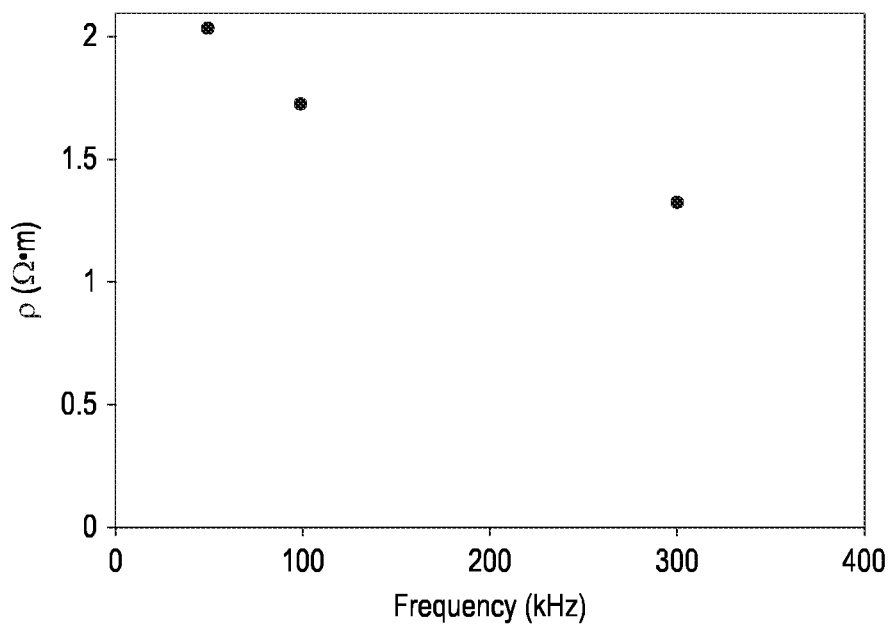
FIG. 16(a) shows results from measurements of electrical resistivity ($\rho$) of a human forearm when the forearm was placed on the face of an air-cored MIS gradiometer probe, using three frequencies (50 kHz, 100 kHz and 300 kHz)
Figure 16B:
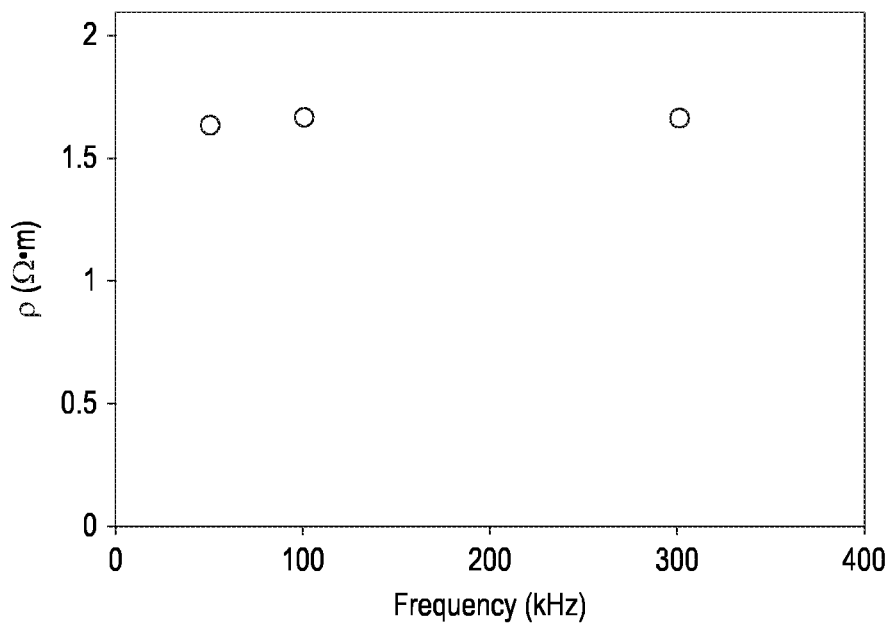
FIG. 16(b) shows results from measurements of electrical resistivity ($\rho$) of a human forearm when the forearm was placed on the face of a ferrite-cored MIS gradiometer probe, using three frequencies (50 kHz, 100 kHz and 300 kHz).

Conductivity measurements were performed on a human forearm with the forearm placed on the face of the air cored and ferrite probes, using the three frequencies 50 kHz, 100 kHz, and 300 kHz. Measurements were repeated 10 times for each frequency. The results are plotted as electrical resistivity (inverse of conductivity) versus frequency as shown in FIG. 16.

DISCUSSION

The above simulation results indicate that the magnetic fields generated by the air cored and ferrite cored further laboratory prototypes are largely contained within and in front of the gap between the ferrite core and the outer cylinder. This significantly screened out the signals from surrounding tissues such as the vaginal wall. The simulations also indicated that the penetration depth for the normalised gradiometer signal were similar for both designs, although less for the ferrite than the air cored probe.

Figure 7:
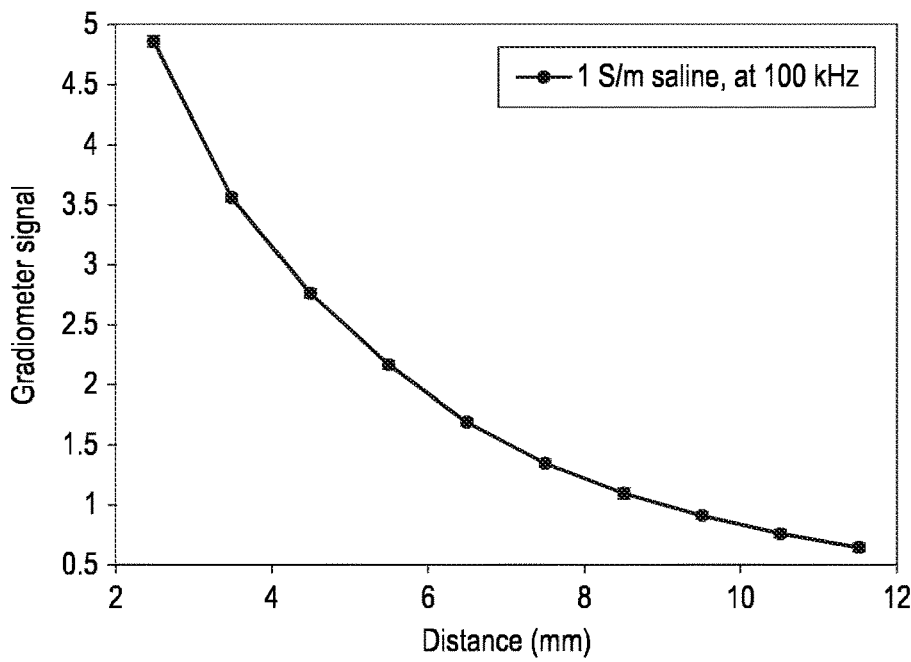
FIG. 7 shows gradiometer signal versus distance.

The experimental measurements using saline containers placed on the gradiometers showed similar sensitivities for the air and ferrite cored transducers. In both cases, sensitivity increased with frequency FIG. 7 shows that sensitivity increases with frequency between kHz and 100 kHz but somewhat less between 100 kHz and 300 kHz. This is probably caused by losses within the coils. The sensitivity of both gradiometers decreases with increasing distance from the probe face, in agreement with the simulations.

The measurements made on the arm show a difference between the two types of gradiometer. The air-cored design is sensitive to tissues at a greater depth than the ferrite cored design.

The results shown that a ferrite cored gradiometer design incorporating an air gap between the core and outer cylinder of ferrite does provide significantly reduced sensitivity to surrounding tissues as opposed to the sensitivity to tissues placed directly in front of the face of the transducer.

Although the above describes use of MIS technology to measure conductivity of cervical tissue, it is anticipated that the apparatus and methods described herein could be used in relation to other types of human or animal tissue. For example, the probes have been shown to be suitable for making conductivity measurements of the human forearm.

The invention claimed is:

1. An apparatus for determining the electrical conductivity of target cervical tissue using magnetic impedance spectroscopy comprising:
   an exciter for producing a magnetic field which is capable of inducing currents in the target cervical tissue;
   a detector for detecting perturbations in said magnetic field caused by said induced currents, the detector including magnetic screen for minimising sensitivity to tissues other than the target cervical tissue;
   a processor for determining an electrical conductivity of said target cervical tissue from said perturbations;
   wherein said exciter and said detector are arranged co-linearly with the target cervical tissue at one end thereof; and
   wherein, in use, the target cervical tissue is not located between said exciter and said detector,
   wherein said exciter is an excitation coil and said detector is a gradiometer; and
   wherein the apparatus further comprises a housing having a face, said housing covered in two aluminised polyester films, and said face patterned in petals.

2. An apparatus for determining the electrical conductivity of target human or animal tissue using magnetic impedance spectroscopy comprising:
   an exciter for producing a magnetic field which is capable of inducing currents in the target human or animal tissue;
   a detector for detecting perturbations in said magnetic field caused by said induced currents, the detector including magnetic screen for minimising sensitivity to tissues other than the target human or animal tissue;
   a processor for determining an electrical conductivity of said target human or animal tissue from said perturbations;
   wherein said exciter and said detector are arranged co-linearly with the target human or animal tissue at one end thereof; and
   wherein, in use, the target human or animal tissue is not located between exciter and said detector,
   wherein said exciter is an excitation coil and said detector is a gradiometer; and
   wherein the apparatus further comprises a housing having a face, said housing covered in two aluminised polyester films, and said face patterned in petals.

3. The apparatus as claimed in claim 1, wherein said gradiometer comprises a magnetoresistive device for detecting perturbations in said magnetic field caused by said induced currents.

4. The apparatus as claimed in claim 1, wherein said gradiometer comprises at least two gradiometer sensing coils for detecting perturbations in said magnetic field caused by said induced currents.

5. The apparatus as claimed in claim 1 wherein said magnetic screen comprises ferrite screening.

6. The apparatus as claimed in claim 1 wherein said magnetic screen further comprises concentric ferrite mouldings.

7. The apparatus as claimed in claim 4 further comprising a ferrite core on which said excitation coil and said gradiometer sensing coils are wound.

8. The apparatus as claimed in claim 1, wherein said excitation coil comprises copper wire of 0.2 mm thickness.

9. The apparatus as claimed in claim 1, wherein said excitation coil comprises 30 turns.

10. The apparatus as claimed in claim 4 wherein said gradiometer sensing coils comprise copper wire of 0.1 mm thickness.

11. The apparatus as claimed in claim 4 wherein said gradiometer sensing coils each comprise 40 turns.

12. The apparatus as claimed in claim 4 wherein the gradiometer sensing coils are equidistant from said excitation coil.

13. The apparatus as claimed in claim 1 wherein a maximum outer diameter of the apparatus is less than 30 mm.

14. The apparatus as claimed in claim 1 further comprising a housing for the exciter and detector, wherein said housing is made from PEEK or machinable ceramic.

15. The apparatus as claimed in claim 1 further comprising a handle and wherein at least part of said processor is contained within said handle.

16. The apparatus as claimed in claim 1 wherein said processor has a sampling rate of 100 million samples per second.

17. A method of determining the electrical conductivity of target human or animal tissue using magnetic impedance spectroscopy apparatus, the method comprising the steps of:
   placing an exciter close to the target human or animal tissue;
   energising said excitation means at an operating frequency in the range of 50 kHz-500 kHz to produce a magnetic field which is capable of inducing currents in the target human or animal tissue;
   using a detector to detect perturbations in said magnetic field caused by said induced currents wherein the detector includes a magnetic screen for minimising sensitivity to tissues other than the target tissue;
   determining an electrical conductivity of said target human or animal tissue from said perturbations;

wherein said exciter and said detector are arranged co-linearly with the target human or animal tissue at one end thereof; and wherein, in use, the target human or animal tissue is not located between said exciter and said detector, wherein said exciter is an excitation coil and said detector is a gradiometer; and wherein the apparatus further comprises housing having a face, said housing covered in two aluminised polyester films, and said face patterned in petals.

18. The apparatus as claimed in claim 4 wherein said apparatus comprises a non-ferritic tube on which said excitation coil and said gradiometer sensing coils are wound, wherein a ferrite core is positioned in said non-ferritic tube.

19. The apparatus as claimed in claim 14 wherein said housing further contains electric field screening made of a metalized polymer film or a conductive paint layer.

20. The apparatus as claimed in claim 18 wherein said non-ferritic tube is a glass tube.

21. The apparatus as claimed in claim 1 wherein the exciter has an operating frequency in the range 50 kHz-500 kHz.

* * * * *